US012379330B1

(12) United States Patent
Viola et al.

(10) Patent No.: US 12,379,330 B1
(45) Date of Patent: Aug. 5, 2025

(54) MULTIFUNCTIONAL HAND SWITCH ASSEMBLY FOR A PORTABLE X-RAY DEVICE

(71) Applicants: FSK Co., Ltd., Gimpo-si (KR); First Source Inc., Rochester, NY (US); Ronald Viola, Pittsford, NY (US); Ju Seon Youn, Seoul (KR); David Venniro, Webster, NY (US); Ha Yeon Youn, Seoul (KR)

(72) Inventors: Ronald Viola, Pittsford, NY (US); Ju Seon Youn, Seoul (KR); David Venniro, Webster, NY (US); Ha Yeon Youn, Seoul (KR)

(73) Assignees: FSK Co., Ltd., Gimpo-si (KR); First Source Inc., Rochester, NY (US); Ronald Viola, Pittsford, NY (US); Ju Seon Youn, Seoul (KR); David Venniro, Webster, NY (US); Ha Yeon Youn, Seoul (KR)

( * ) Notice: Subject to any disclaimer, the term of this patent is extended or adjusted under 35 U.S.C. 154(b) by 0 days.

(21) Appl. No.: 19/081,465

(22) Filed: Mar. 17, 2025

(30) Foreign Application Priority Data

Mar. 18, 2024 (KR) ........................ 10-2024-0037057

(51) Int. Cl.
*G01N 23/04* (2018.01)
(52) U.S. Cl.
CPC ..... *G01N 23/04* (2013.01); *G01N 2223/1016* (2013.01); *G01N 2223/301* (2013.01); *G01N 2223/308* (2013.01)
(58) Field of Classification Search
CPC ........... G01N 23/04; G01N 2223/1016; G01N 2223/301; G01N 2223/308
See application file for complete search history.

(56) References Cited

U.S. PATENT DOCUMENTS 10,842,449 B2    11/2020 Diaz Carmena et al.

FOREIGN PATENT DOCUMENTS

KR          10-0596652 B1    7/2006
KR    10-2018-0060248 A    6/2018

OTHER PUBLICATIONS

KR-10-2018-0060248 (Year: 2018).*
Korean Office Action of No. 10-2024-0037057 dated May 16, 2024.
Korean Written Decision of Registration of No. 10-2024-0037057 dated Sep. 30, 2024.

* cited by examiner

Primary Examiner — Courtney D Thomas
(74) Attorney, Agent, or Firm — Sughrue Mion, PLLC

(57) ABSTRACT

Disclosed is a multi-function hand switch assembly for a portable x-ray device attached to and detached from a portable x-ray device having handle binders formed on both side surfaces and detachably fixes a hand switch extending as a cable from one side surface of the portable x-ray device, including a handle portion detachably bound to the handle binders to be able to rotate a predetermined angle about the handle binders and extending to surround both side surfaces and an upper portion of the portable x-ray device; a bracket portion detachably bound to a center of an upper surface of the handle portion, fixed to be able to rotate in place at the center of the upper surface of the handle portion, and extending a predetermined height upward; and a holder portion integrally formed with an upper end of a bracket and allowing the hand switch to be inserted or withdrawn.

3 Claims, 6 Drawing Sheets

MULTIFUNCTIONAL HAND SWITCH ASSEMBLY FOR A PORTABLE X-RAY DEVICE

CROSS-REFERENCE TO RELATED APPLICATION

This application claims priority to and the benefit of Korean Patent Application No. 10-2024-0037057, filed on Mar. 18, 2024, the disclosure of which is incorporated herein by reference in its entirety.

BACKGROUND

1. Field of the Invention

The present invention relates to a multi-function hand switch assembly, and more particularly, to a multi-function hand switch assembly with a structure mounted on a portable x-ray device.

2. Discussion of Related Art

Conventionally, x-ray devices have been classified into a stationary type and a portable type depending on whether the device can be carried and moved. However, a portable x-ray device is an x-ray device that can literally be carried around rather than simply being movable.

In addition, a controller controlling a conventional x-ray imaging device has a structure that allows a tube voltage caused by an input voltage regulator to be constantly controlled, allows direct or indirect imaging to be selected as necessary, allows a dose of x-rays to be appropriately set according to physical conditions of a subject, and controls a numbering display means to be distinguished.

As illustrated in FIG. 1, in the case of an x-ray imaging device according to the related art, a holder that can hold a hand switch on a specific portion is mounted.

However, since the holder of the x-ray imaging device according to the related art is fixed to a specific position, there is a problem in that, for a user to use the hand switch, the user needs to reach for that portion and withdraw the hand switch.

Accordingly, there is a need for technology that can address the above-mentioned problem according to the related art.

RELATED ART DOCUMENT

Patent Document (Patent document 1) Korean Patent Registration No. 10-0596652 (Date of Registration: Jun. 27, 2006)

SUMMARY OF THE INVENTION

The present invention is directed to providing a multi-function hand switch assembly for a portable x-ray device in which a hand switch can be easily and stably attached to and detached from one side surface of the portable x-ray device and the hand switch can be attached and detached at various positions and in various directions, thereby allowing an x-ray imaging task to be performed more conveniently and stably.

According to an aspect of the present invention, there is provided a multi-function hand switch assembly that is operated by being attached to and detached from a portable x-ray device having handle binders formed on both side surfaces and detachably fixes a hand switch extending as a cable from one side surface of the portable x-ray device, the multi-function hand switch assembly including: a handle portion detachably bound to the handle binders to be able to rotate a predetermined angle about the handle binders and extending to surround both side surfaces and an upper portion of the portable x-ray device; a bracket portion detachably bound to a center of an upper surface of the handle portion, fixed to be able to rotate in place at the center of the upper surface of the handle portion, and extending a predetermined height upward; and a holder portion integrally formed with an upper end of a bracket and allowing the hand switch to be inserted or withdrawn.

In one embodiment of the present invention, the handle portion may include: a hinge binding portion detachably bound to the handle binders formed on both side surfaces of the portable x-ray device; a handle main body portion extending to surround both side surfaces and an upper surface of the portable x-ray device and forming a C-shaped structure in a plan view; and a bracket attachment/detachment portion mounted on both side surfaces and an upper surface of the handle main body portion, detachably mounting the bracket portion, and fixing the bracket portion in a manner in which the bracket portion is able to rotate in place.

In one embodiment of the present invention, the bracket portion may include: a sliding binding member that is able to be fixed after sliding and being inserted into the bracket attachment/detachment portion or separated therefrom after sliding and being discharged; an extending main body portion that has the sliding binding member mounted on a lower surface and that extends toward one side, is bent upward, and then extends to form a C-shaped frame structure that is able to be held by a human hand placed therein; and a binding fixing member that is mounted on a lower portion of the extending main body portion, fastens the sliding binding member using a bolt, and binds and fixes the sliding binding member and the bracket attachment/detachment portion to each other by a tightening operation.

In one embodiment of the present invention, the holder portion may include: a holder side surface portion integrally formed with an upper end of the extending main body portion and extending toward one side to form a space into which the hand switch is able to be inserted; a plurality of holder side surface through-holes formed to be spaced at predetermined intervals in the holder side surface portion and allowing communication between the inside and the outside of the holder portion; and a holder side surface slit groove formed in an upper surface of the holder side surface portion, extending a predetermined length from an inlet through which the hand switch is inserted, and formed to allow the communication between the inside and the outside of the holder portion.

In one embodiment of the present invention, the holder side surface portion of the holder portion may form an inclined surface structure that is tilted a predetermined angle toward the inside of the holder portion and may be formed of a material having an elastic restoration force of a predetermined magnitude to press a side surface of the hand switch with a pressure of a predetermined magnitude and fix the hand switch.

BRIEF DESCRIPTION OF THE DRAWINGS

The above and other objects, features, and advantages of the present invention will become more apparent to those of ordinary skill in the art by describing exemplary embodiments thereof in detail with reference to the accompanying drawings, in which.

DETAILED DESCRIPTION OF EXEMPLARY EMBODIMENTS

Hereinafter, exemplary embodiments of the present invention will be described in detail with reference to the accompanying drawings. Prior to this, terms or words used in the present specification and claims should not be construed as being limited to general or dictionary meanings and should be interpreted with meanings and concepts consistent with the technical spirit of the present invention.

Throughout the present specification, when a certain member is described as being located "on" another member, this includes not only a case in which the member is in contact with the other member, but also a case in which another member is present between the two members. Throughout the present specification, when a certain part is described as "including" a certain component, unless particularly described otherwise, this means that the part may further include other components instead of excluding other components.

Figure 1:
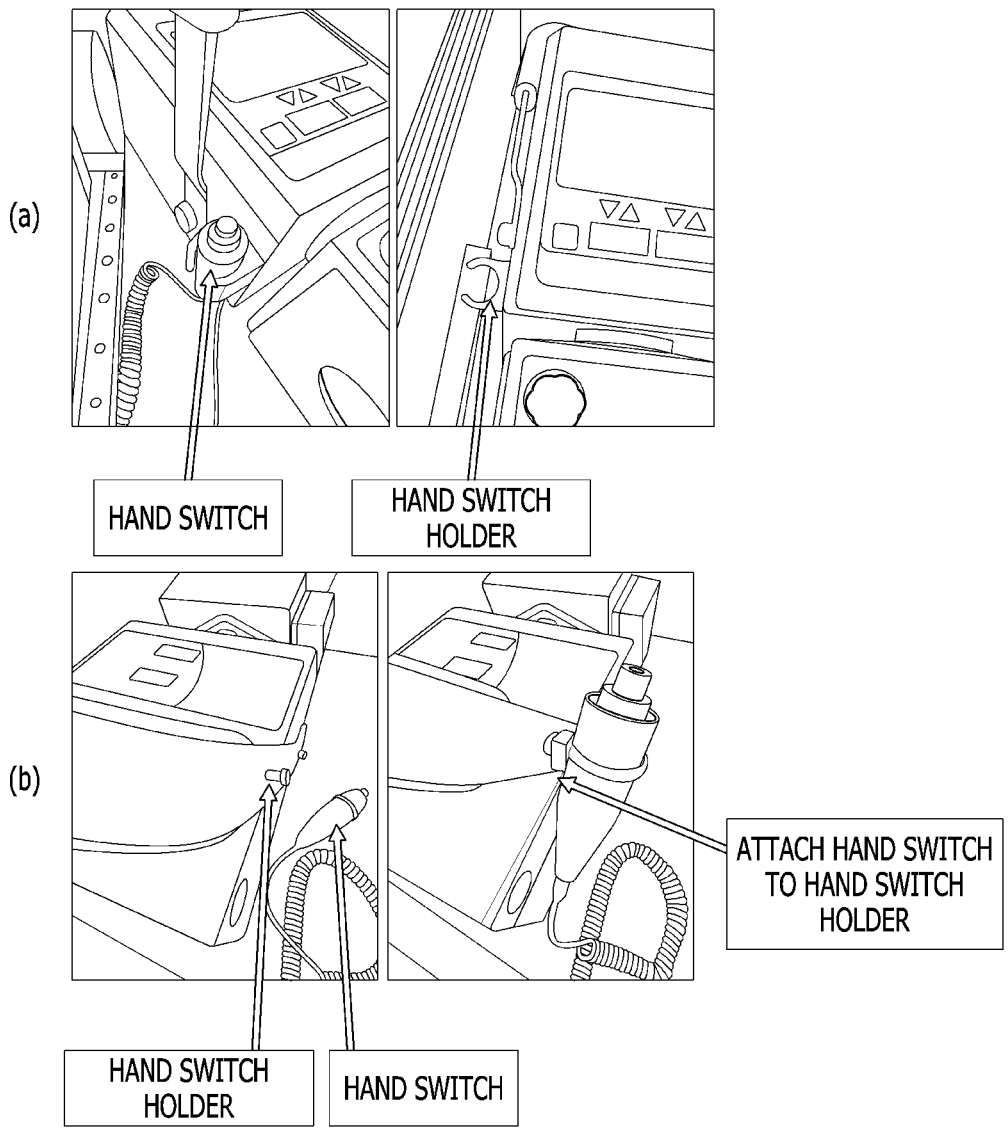
FIG. 1 shows images of a hand switch fixing structure for a portable x-ray device according to the related art.
Figure 2:
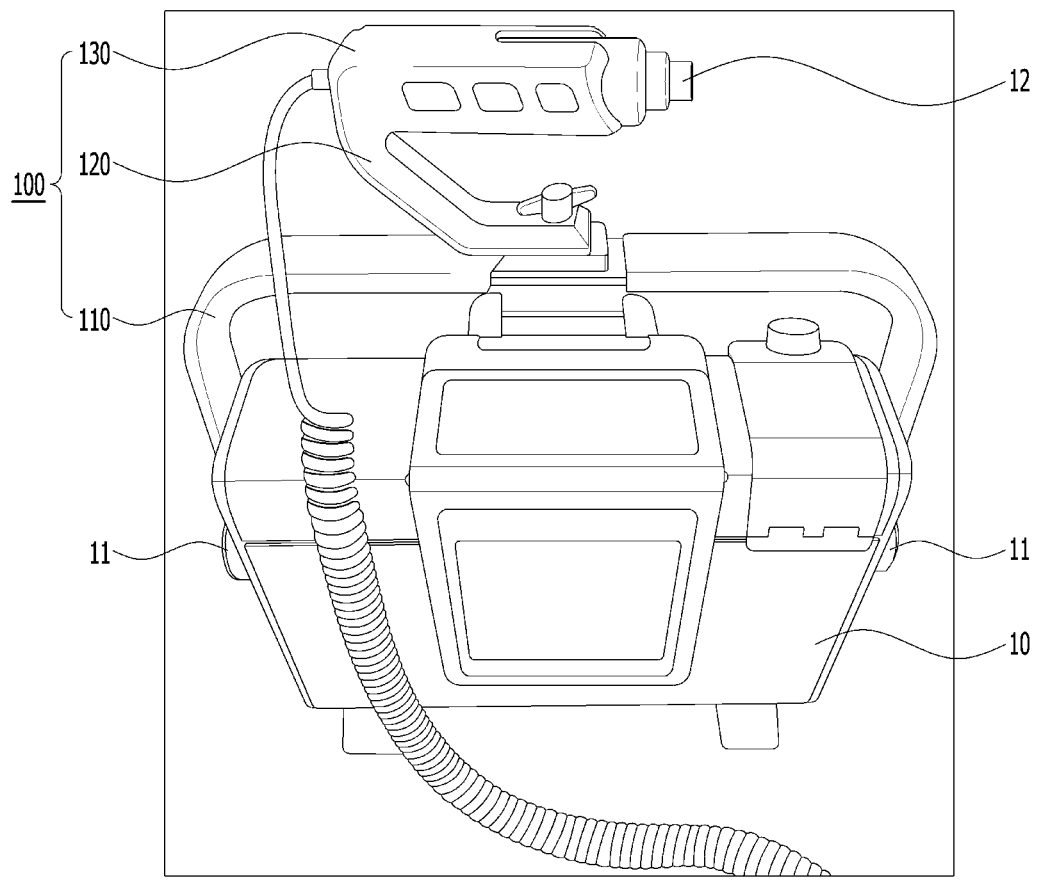
FIG. 2 is an image of a multi-function hand switch assembly according to one embodiment of the present invention.
Figure 3:
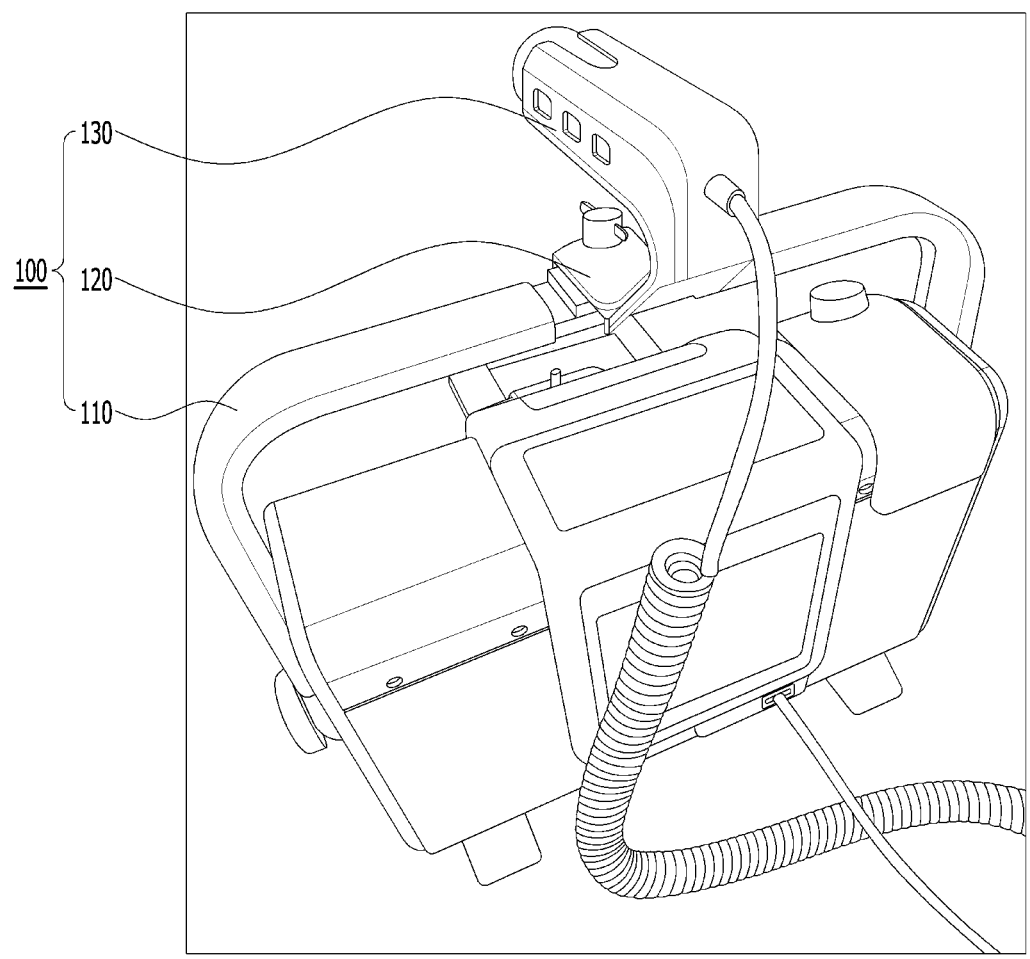
FIG. 3 is an image of the multi-function hand switch assembly according to one embodiment of the present invention.
Figure 4:
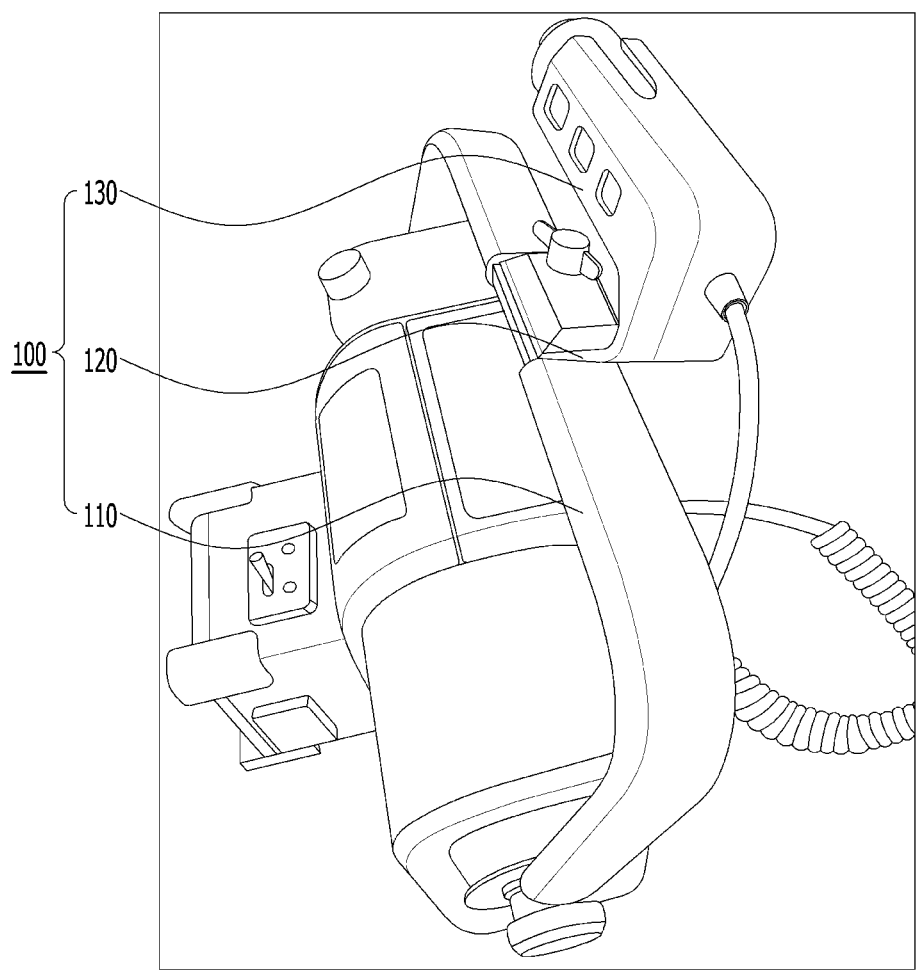
FIG. 4 is an image of the multi-function hand switch assembly according to one embodiment of the present invention.
Figure 5:
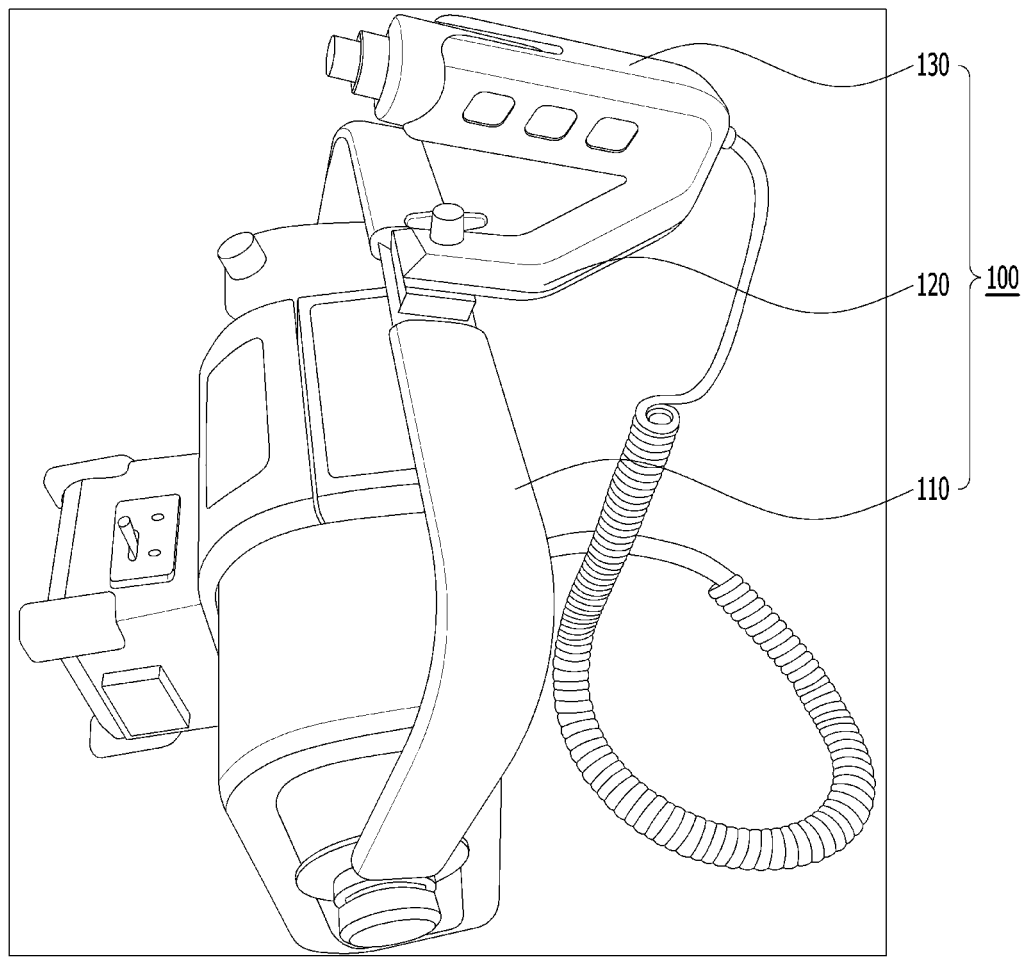
FIG. 5 is an image of the multi-function hand switch assembly according to one embodiment of the present invention.
Figure 6:
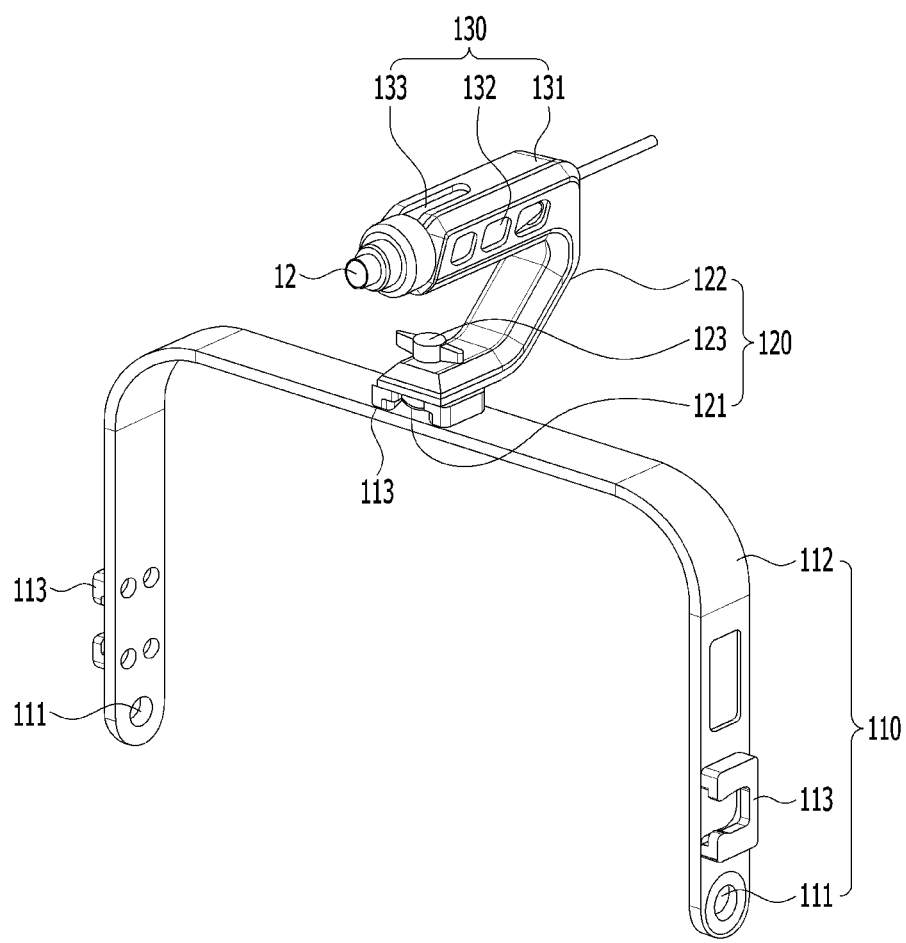
FIG. 6 is a perspective view illustrating the multi-function hand switch assembly of the present invention.

Images of a multi-function hand switch assembly according to one embodiment of the present invention are shown in FIGS. 2 to 5, and a perspective view of the multi-function hand switch assembly of the present invention is illustrated in FIG. 6.

Referring to these drawings, a multi-function hand switch assembly 100 according to the present embodiment is a multi-function hand switch assembly that is operated by being attached to and detached from a portable x-ray device having handle binders formed on both side surfaces and detachably fixes a hand switch extending as a cable from one side surface of the portable x-ray device, and the multi-function hand switch assembly 100 includes a handle portion 110, a bracket portion 120, and a holder portion 130 each having a specific structure and through which the hand switch can thus be easily and stably attached to and detached from one side surface of the portable x-ray device and the hand switch can be attached and detached at various positions and in various directions, thereby allowing an x-ray imaging task to be performed more conveniently and stably.

Hereinafter, each component constituting the multi-function hand switch assembly 100 according to the present embodiment will be described in detail with reference to the drawings.

The handle portion 110 according to the present embodiment is detachably bound to handle binders 11, is bound to be able to rotate a predetermined angle about the handle binders 11, and extends to surround both side surfaces and an upper portion of the portable x-ray device.

Specifically, the handle portion 110 may be a component including a hinge binding portion 111, a handle main body portion 112, and a bracket attachment/detachment portion 113 each having a specific structure. The hinge binding portion 111 of the handle portion 110 is detachably bound to the handle binders 11 formed on both side surfaces of the portable x-ray device. The handle main body portion 112 of the handle portion 110 extends to surround both side surfaces and an upper surface of the portable x-ray device and forms a C-shaped structure in a plan view. The bracket attachment/detachment portion 113 of the handle portion 110 is mounted on both side surfaces and an upper surface of the handle main body portion 112, detachably mounts the bracket portion 120, and fixes the bracket portion 120 in a manner in which the bracket portion 120 is able to rotate in place.

The bracket portion 120 according to the present embodiment is detachably bound to a center of an upper surface of the handle portion 110, is fixed to be able to rotate in place at the center of the upper surface of the handle portion 110, and extends a predetermined height upward.

Specifically, the bracket portion 120 may be a component including a sliding binding member 121, an extending main body portion 122, and a binding fixing member 123 each having a specific structure. The sliding binding member 121 of the bracket portion 120 is able to be fixed after sliding and being inserted into the bracket attachment/detachment portion 113 or separated therefrom after sliding and being discharged. The extending main body portion 122 of the bracket portion 120 has the sliding binding member 121 mounted on a lower surface and extends toward one side, is bent upward, and then extends to form a C-shaped frame structure that is able to be held by a human hand placed therein. In addition, the binding fixing member 123 of the bracket portion 120 is mounted on a lower portion of the extending main body portion 122, fastens the sliding binding member 121 using a bolt, and binds and fixes the sliding binding member 121 and the bracket attachment/detachment portion 113 to each other by a tightening operation.

The holder portion 130 according to the present embodiment is integrally formed with an upper end of a bracket and allows a hand switch 12 to be inserted or withdrawn.

Specifically, the holder portion 130 may be a component including a holder side surface portion 131, a plurality of holder side surface through-holes 132, and a holder side surface slit groove 133 each having a specific structure. The holder side surface portion 131 of the holder portion 130 is integrally formed with an upper end of the extending main body portion 122 and extends toward one side to form a space into which the hand switch 12 is able to be inserted. The plurality of holder side surface through-holes 132 are formed to be spaced at predetermined intervals in the holder side surface portion 131 and allow communication between the inside and the outside of the holder portion 130. The holder side surface slit groove 133 of the holder portion 130 is formed in an upper surface of the holder side surface portion 131, extends a predetermined length from an inlet through which the hand switch 12 is inserted, and is formed to allow the communication between the inside and the outside of the holder portion 130.

In some cases, the holder side surface portion 131 of the holder portion 130 may form an inclined surface structure that is tilted a predetermined angle toward the inside of the holder portion 130 and may be formed of a material having an elastic restoration force of a predetermined magnitude to press a side surface of the hand switch 12 with a pressure of a predetermined magnitude and fix the hand switch 12.

In some cases, the hand switch 12 mentioned above may be configured as a wired device, and after the hand switch 12 is removed, the holder portion 130 itself may be converted into a wireless switch (so that x-ray exposure using a portable (handheld) x-ray generator with Bluetooth is possible).

As described above, by including the handle portion 110, the bracket portion 120, and the holder portion 130 each having a specific structure, in the multi-function hand switch assembly for a portable x-ray device of the present invention, the hand switch 12 can be easily and stably attached to and detached from one side surface of the portable x-ray device and the hand switch 12 can be attached and detached at various positions and in various directions, thereby allowing an x-ray imaging task to be performed more conveniently and stably.

As described above, the present invention can provide a multi-function hand switch assembly for a portable x-ray device that includes a handle portion, a bracket portion, and a holder portion each having a specific structure and thus a hand switch can be easily and stably attached to and detached from one side surface of the portable x-ray device and the hand switch can be attached and detached at various positions and in various directions, thereby allowing an x-ray imaging task to be performed more conveniently and stably.

In the detailed description of the present invention given above, only some embodiments according to the present invention have been described. However, the present invention should not be understood as being limited to the embodiments mentioned in the detailed description above, and on the contrary, the present invention should be understood as including all modifications, equivalents, and substitutes within the spirit and scope of the present invention defined by the appended claims.

That is, the present invention is not limited to the specific embodiments described above or the description given above, those of ordinary skill in the art to which the present invention pertains can make various modifications without departing from the gist of the present invention claimed in the claims, and such modifications also belong to the protection scope of the present invention.

What is claimed is:

1. A multi-function hand switch assembly that is operated by being attached to and detached from a portable x-ray device (10) having handle binders (11) formed on both side surfaces and detachably fixes a hand switch (12) extending as a cable from one side surface of the portable x-ray device (10), the multi-function hand switch assembly comprising:
    a handle portion (110) detachably bound to the handle binders (11) to be able to rotate a predetermined angle about the handle binders (11) and extending to surround both side surfaces and an upper portion of the portable x-ray device;
    a bracket portion (120) detachably bound to a center of an upper surface of the handle portion (110), fixed to be able to rotate in place at the center of the upper surface of the handle portion (110), and extending a predetermined height upward; and
    a holder portion (130) integrally formed with an upper end of a bracket and allowing the hand switch (12) to be inserted or withdrawn,
    wherein the handle portion (110) includes a hinge binding portion (111) detachably bound to the handle binders (11) formed on both side surfaces of the portable x-ray device, a handle main body portion (112) extending to surround both side surfaces and an upper surface of the portable x-ray device and forming a C-shaped structure in a plan view, and a bracket attachment/detachment portion (113) mounted on both side surfaces and an upper surface of the handle main body portion (112), detachably mounting the bracket portion (120), and fixing the bracket portion (120) in a manner in which the bracket portion (120) is able to rotate in place, and
    the bracket portion (120) includes a sliding binding member (121) that is able to be fixed after sliding and being inserted into the bracket attachment/detachment portion (113) or separated therefrom after sliding and being discharged, an extending main body portion (122) that has the sliding binding member (121) mounted on a lower surface and that extends toward one side, is bent upward, and then extends to form a C-shaped frame structure that is able to be held by a human hand placed therein, and a binding fixing member (123) that is mounted on a lower portion of the extending main body portion (122), fastens the sliding binding member (121) using a bolt, and binds and fixes the sliding binding member (121) and the bracket attachment/detachment portion (113) to each other by a tightening operation.

2. The multi-function hand switch assembly of claim 1, wherein the holder portion (130) includes:
    a holder side surface portion (131) integrally formed with an upper end of the extending main body portion (122) and extending toward one side to form a space into which the hand switch (12) is able to be inserted;
    a plurality of holder side surface through-holes (132) formed to be spaced at predetermined intervals in the holder side surface portion (131) and allowing communication between the inside and the outside of the holder portion (130); and
    a holder side surface slit groove (133) formed in an upper surface of the holder side surface portion (131), extending a predetermined length from an inlet through which the hand switch (12) is inserted, and formed to allow the communication between the inside and the outside of the holder portion (130).

3. The multi-function hand switch assembly of claim 2, wherein the holder side surface portion (131) of the holder portion (130) forms an inclined surface structure that is tilted a predetermined angle toward the inside of the holder portion (130) and is formed of a material having an elastic restoration force of a predetermined magnitude to press a side surface of the hand switch (12) with a pressure of a predetermined magnitude and fix the hand switch (12).

\* \* \* \* \*